(12) United States Patent
Carter et al.

(10) Patent No.: US 7,691,055 B2
(45) Date of Patent: Apr. 6, 2010

(54) ENDOSCOPIC APPARATUS HAVING AN IMPROVED ELEVATOR

(75) Inventors: Matthew P. Carter, Dobson, NC (US); Gregory J. Skerven, Kernersville, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 307 days.

(21) Appl. No.: 11/404,554

(22) Filed: Apr. 14, 2006

(65) Prior Publication Data

US 2006/0235271 A1    Oct. 19, 2006

Related U.S. Application Data

(60) Provisional application No. 60/671,951, filed on Apr. 15, 2005, provisional application No. 60/779,181, filed on Mar. 3, 2006, provisional application No. 60/799,182, filed on Mar. 3, 2006.

(51) Int. Cl.
    *A61B 1/00* (2006.01)
(52) U.S. Cl. ........................... 600/107; 600/106
(58) Field of Classification Search ............... 600/107, 600/104, 106; 604/166.01
    See application file for complete search history.

(56) References Cited

U.S. PATENT DOCUMENTS

| | | | |
|---|---|---|---|
| 4,407,273 A | 10/1983 | Ouchi | |
| 4,452,236 A * | 6/1984 | Utsugi | 600/107 |
| 5,343,853 A | 9/1994 | Komi | |
| 5,386,818 A | 2/1995 | Schneebaum et al. | |
| 5,460,168 A * | 10/1995 | Masubuchi et al. | 600/123 |
| 5,569,157 A * | 10/1996 | Nakazawa et al. | 600/107 |
| 5,707,344 A | 1/1998 | Nakazawa et al. | |
| 5,820,546 A | 10/1998 | Ouchi | |
| 5,899,850 A | 5/1999 | Ouchi | |
| 5,921,971 A | 7/1999 | Agro et al. | |
| 5,938,586 A | 8/1999 | Wilk et al. | |
| 6,582,357 B2 * | 6/2003 | Ouchi et al. | 600/107 |
| 6,605,033 B1 * | 8/2003 | Matsuno | 600/107 |
| 6,827,683 B2 | 12/2004 | Otawara | |
| 7,087,010 B2 * | 8/2006 | Ootawara et al. | 600/104 |
| 2002/0091303 A1 | 7/2002 | Ootawara et al. | |

* cited by examiner

*Primary Examiner*—Linda C Dvorak
*Assistant Examiner*—Alireza Nia
(74) *Attorney, Agent, or Firm*—Brinks Hofer Gilson & Lione

(57) ABSTRACT

A grasping apparatus for use with an elevator of an endoscope having enhanced grasping features for grasping an elongate medical device is disclosed. The apparatus comprises a body comprising a grasping surface and an opening formed through the grasping surface to receive the elevator. The opening of the body is configured to be disposed about the elevator of the endoscope. The grasping surface is configured to be disposed on the elevator for grasping of the elongate medical device.

18 Claims, 6 Drawing Sheets

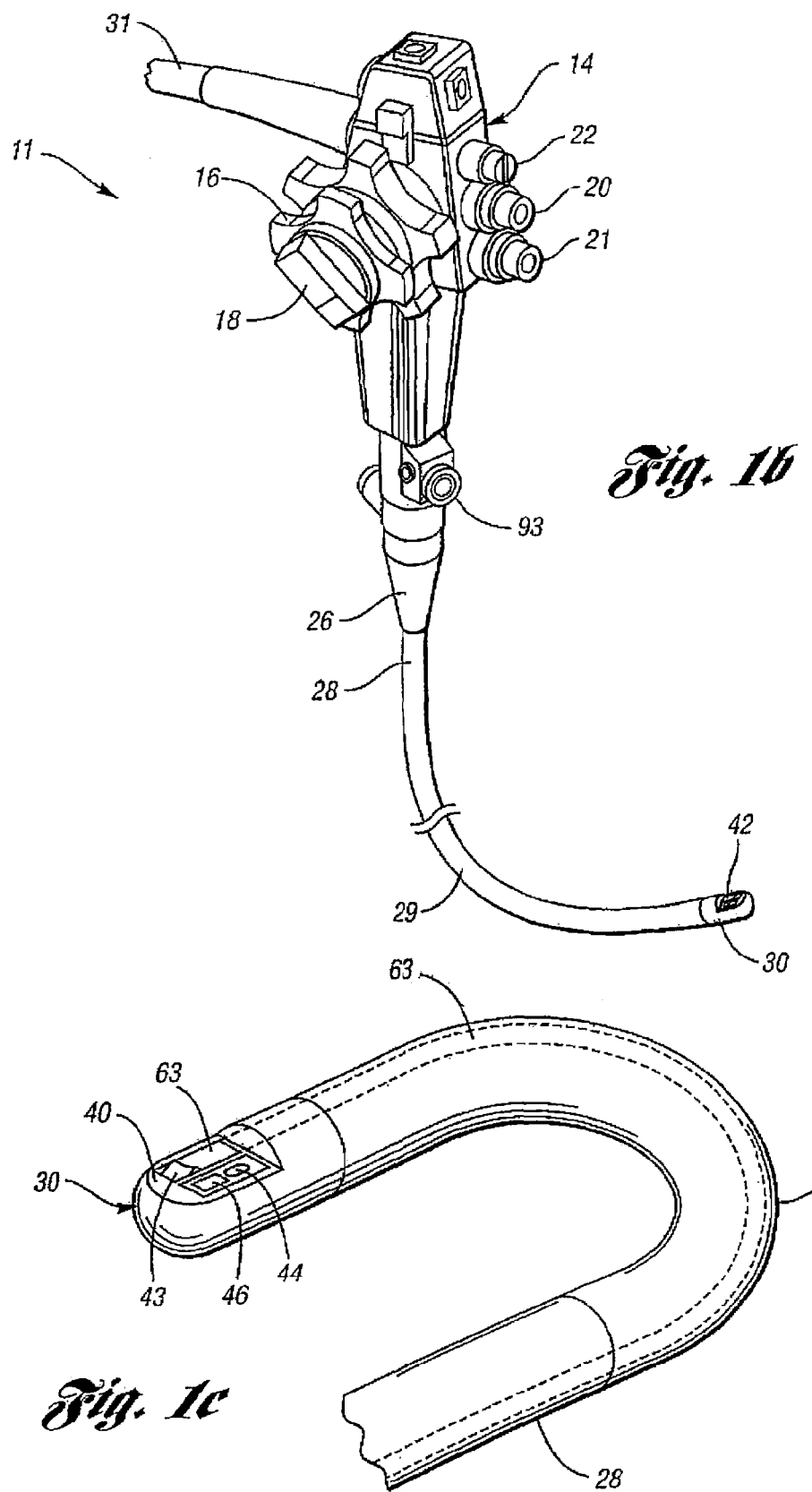

ENDOSCOPIC APPARATUS HAVING AN IMPROVED ELEVATOR

CROSS-REFERENCE TO RELATED APPLICATIONS

This application claims the benefit of U.S. Provisional Application No. 60/671,951, filed on Apr. 15, 2005, entitled "IMPROVED ENDOSCOPE," the entire contents of which are incorporated herein by reference.

This application also claims the benefit of U.S. Provisional Application No. 60/779,181, filed on Mar. 3, 2006, entitled "ENDOSCOPE HAVING AN ELEVATOR WITH A GRASPING TIP," the entire contents of which are incorporated herein by reference.

This application also claims the benefit of U.S. Provisional Application No. 60/779,182, filed on Mar. 3, 2006, entitled "ENDOSCOPIC ELEVATOR APPARATUS HAVING A POLYMERIC ELEVATOR WITH A GRASPING SLOT," the entire contents of which are incorporated herein by reference.

FIELD OF THE INVENTION

The present invention relates to medical devices, and more particularly, to endoscopes having a medical instrument elevator.

BACKGROUND OF THE INVENTION

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

Many current endoscopic systems include endoscopes having an elevator used to orient the wire guide and to lock the distal end of the wire guide. In many of such endoscopes, the elevator includes a v-shaped groove. The v-shaped groove is typically used to guide the wire guide to a central position relative to the endoscope. The elevator having a v-shaped groove is further used to lock the distal end of the guide wire.

Endoscopes using a rigid elevator lock and/or a v-shaped groove arrangement, however, may be improved. For example, in many situations, the elevator may tear, scrape, or otherwise affect wire guides or other instruments used therewith. This is particular with soft, Teflon™-coated wire guides. When such wire guides are positioned within the v-shaped groove of the elevator, even slight axial movement of the wire guide may result in a torn, scraped, stripped or damaged wire guide. Such result to a wire guide may undesirably require replacing the wire guide during the procedure. This, in turn, undesirably lengthens the overall procedure time and may be costly.

Many other endoscopes are provided with rigid, flat-edged elevators. One challenge is that wire guide orientation is difficult to control with flat-edged elevators. Specifically, the wire guide tends to move from side to side relative to the elevator, thereby challenging the physician to insert the wire guide into a target anatomy. Moreover, when flat-edged elevators are used to lock the distal end of an instrument, tearing, scraping, stripping or other undesirable damaged effect on the instrument can also result.

Another issue is that during use the elevator may compress elongate devices such as catheters, thereby preventing the passage of fluids therethrough or impeding the operation of the catheter device.

Thus, there is a need for an elevator design that reduces the risk of tearing, scraping, stripping or other damaging of devices (e.g., wire guides or catheter) during deployment in a body vessel and allows flow of fluid therethrough during use.

BRIEF SUMMARY OF THE INVENTION

The embodiments of the present invention provide an endoscopic elevator system and an endoscopis assembly having enhanced features for grasping of a medical device, e.g., a catheter or wire guide. The present invention solves some of the current challenges in the endoscope industry. That is, embodiments of the present invention provide a way, during an endoscopic procedure, to maintain a relatively firm grasp of the medical device while reducing (or at least without compromising) the risk of scraping, tearing, stripping or other damage to the medical device.

In one embodiment, the present invention provides a grasping apparatus for use with an elevator of an endoscope having enhanced grasping features for grasping an elongate medical device. The apparatus comprises a body comprising a grasping surface and an opening formed through the grasping surface to receive the elevator. The opening of the body is configured to be disposed about the elevator of the endoscope. The grasping surface is configured to be disposed on the elevator for grasping of the elongate medical device.

In another embodiment, the present invention provides an endoscopic grasping assembly for an endoscope having enhanced features for grasping and reducing damage of an elongate medical device. The assembly comprises an insertion tube extending to a distal tip having an elevator and a control system in communication with the insertion tube and the elevator for movement of the insertion tube and elevator during operation of the endoscope. The assembly further comprises a body comprising a grasping surface and an opening formed through the grasping surface to receive the elevator. The opening of the body is disposed about the elevator of the endoscope. The grasping surface is disposed on the elevator for grasping of the elongate medical device.

In still another embodiment, the present invention provides an endoscopic grasping assembly for an endoscope having enhanced features for grasping and reducing damage of a medical device. The assembly comprises an insertion tube extending to a distal tip having an elevator and a control system. The control system is in communication with the insertion tube and the elevator for movement of the insertion tube and elevator during operation of the endoscope. The assembly further comprises a grasping tip cooperable with the elevator. The grasping tip comprises a body and an opening formed thereon. The body is configured to be disposed on the elevator for enhanced grasping of the medical device.

In yet another embodiment, the present invention provides an endoscopic apparatus having enhanced features for receiving an elongate medical device. The endoscopic apparatus comprises an elevator having a grasping slot formed therethrough and defined by an inner surface. The inner surface has at least one grasping member formed thereon and projects into the grasping slot. The slot is configured to receive the elongate medical device. The grasping member is configured for enhanced grasping of the elongate medical device.

Further objects, features, and advantages of the present invention will become apparent from consideration of the following description and the appended claims when taken in connection with the accompanying drawings.

BRIEF DESCRIPTION OF THE DRAWINGS

FIG. 1b is a perspective view of the endoscope depicted in FIG. 1A;

FIG. 1c is an elevated view of a distal tip of the endoscope in accordance with one embodiment of the present invention;

DETAILED DESCRIPTION OF THE INVENTION

The present invention generally provides an endoscopic elevator and an endoscopic assembly having enhanced features of grasping and reduced scraping of a medical device. Embodiments of the present invention allow a practitioner to relatively firmly grasp the medical device within an endoscope, while reducing the risk of scraping, tearing, or stripping or other damage to the medical device (e.g., catheter, wire guide). In one embodiment, an endoscopic elevator comprises a grasping tip having a body with ridges formed thereon. The ridges are preferably made of polymeric or elastomeric material to engage and receive the medical device, lessening the risk of undesirably scraping thereof.

Figure 1A:
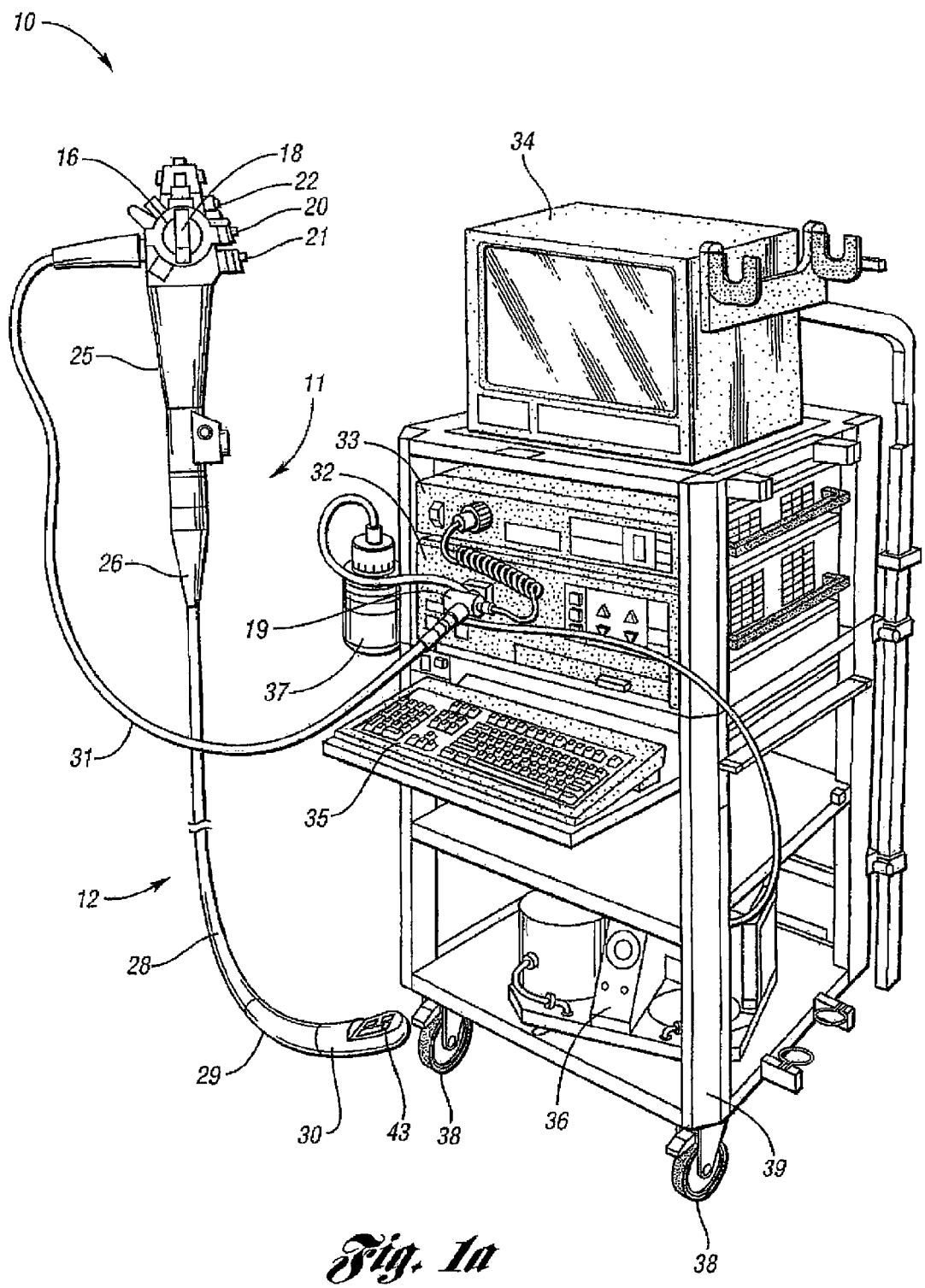
FIG. 1a is a perspective view of an endoscopic system comprising an endoscope in accordance with one embodiment of the present invention.
Figure 2:
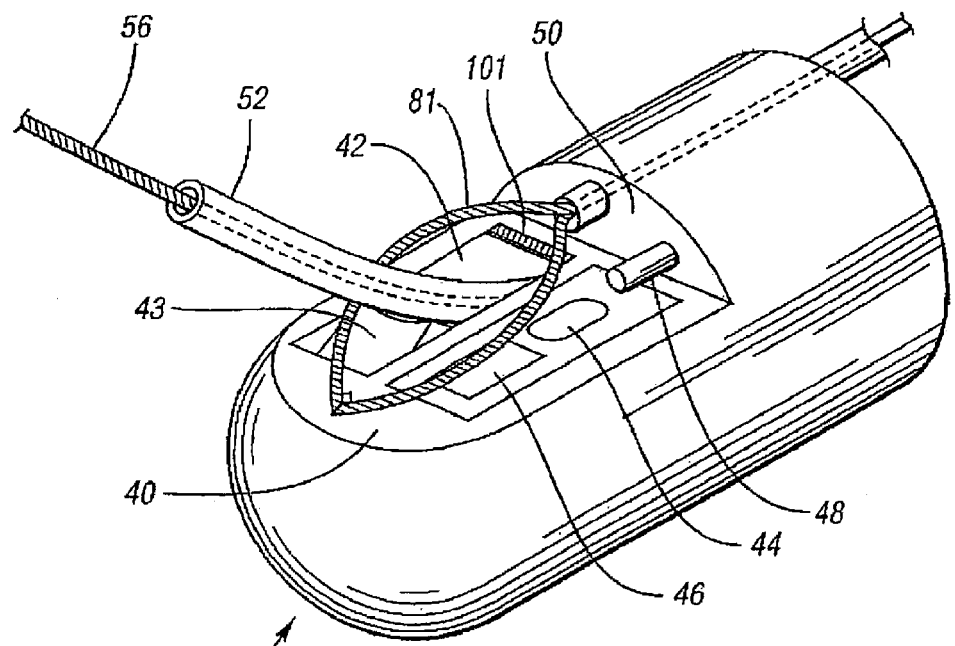
FIG. 2 is an enlarged view of the distal tip of the endoscope in accordance with one embodiment of the present invention.
Figure 3:
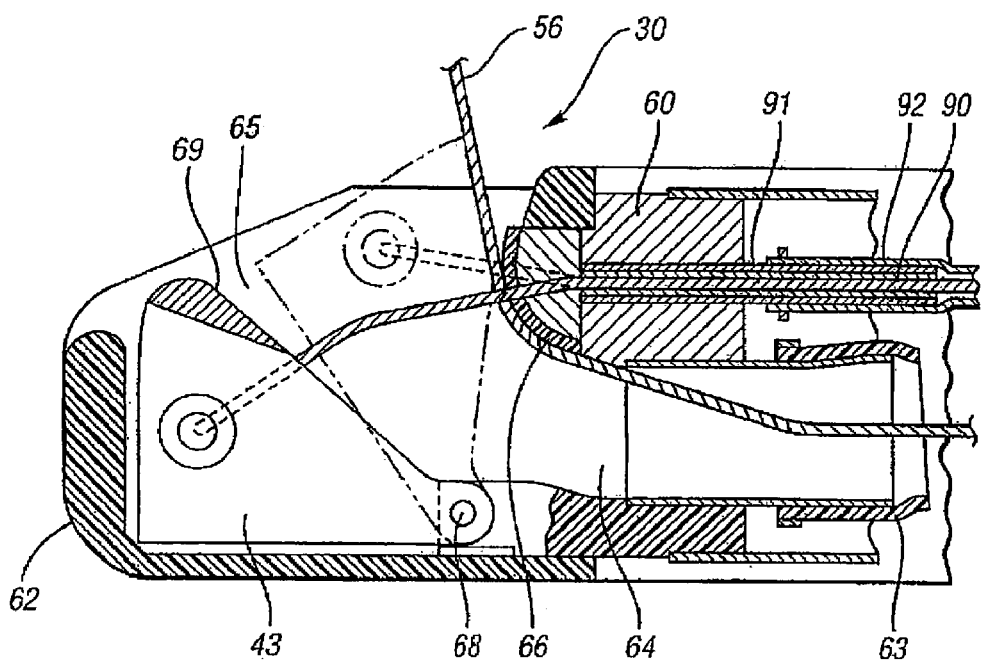
FIG. 3 is a cross-sectional view of the distal tip of the endoscope insertion portion of the endoscope taken along line 3-3.

FIGS. 1-3 illustrate an endoscopic system comprising an endoscope having an elevator with a distal tip. Additional details relating to the endoscopic system are described in U.S. Pat. No. 6,827,683, entitled "ENDOSCOPE SYSTEM AND MEDICAL TREATMENT METHOD" issued Dec. 7, 2004 to Takashi Otawara, which is incorporated herein by reference in its entirety.

FIG. 1a illustrates an endoscopic system 10 comprising an endoscope 11 in accordance with one embodiment of the present invention. In this embodiment, the endoscope 11 comprises an insertion tube 12 to be inserted into a body cavity for various endoscopic procedures including gastroscopy, sigmoidoscopy and colonoscopy, esophago gastro duodenoscopy (EGD), endoscopic retrograde cholangiopancreatography (EROP), and bronchoscopy. As shown, the endoscope 11 comprises an insertion tube 12 having a plurality of channel ports through which endoscopic units may be disposed. In one embodiment, endoscopic units disposed in one of the ports may include one embodiment of an improved elevator having a tip.

As shown in FIGS. 1a and 1b, the endoscope 11 further includes a control system 14 that is in mechanical and fluid communication with the insertion tube 12. The control system 14 is configured to control the insertion tube 12 and endoscopic parts disposed therein. As shown, the control system 14 includes first and second control knobs 16, 18. The control knobs 16, 18 are configured to be in mechanical communication with the insertion tube 12. The control knobs 16, 18 allow the physician to control and guide, by known means, the insertion tube 12 through vessels and cavities of a patient. The control system 14 further includes valve switches (e.g., suction valve 20, air/water valve 21, camera valve 22), each of which are in communication to one of the channel ports of the insertion tube 12. For example, the suction valve switch 20, when activated, allows a vacuum from a suction source through a suction channel port for suctioning unwanted plaque and debris from the patient. In one example, the distal end of the insertion tube 12 is inserted, rectally or orally, to a predetermined endoscopic location within a patient. Insertion of the insertion tube 12 may be rectally or orally depending on the endoscopic procedure. The endoscope in combination with the elevator having the tip reduce the risk of damage, e.g., tearing or scraping, of the wire guide.

In this embodiment, the insertion tube 12 comprises an operating portion 25 connected to the control system 14 and extending to an insertion portion protecting member 26. A control system 14 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connected to the flexure 29. A universal cord 31, on one end, is connected and in communication with the control system 14. On the other end, the cord 31 has a connector 19 attached thereto. The connector 19 is in communication to a light guide tube and electrical contact, and is connected to a light source apparatus 32 and an image processing apparatus 33 (external devices). These external devices may include a monitor 34, an input keyboard 35, a suction pump apparatus 36, and an irrigation bottle 37, and other suitable apparatuses are installed on a rack 39 equipped with carriers 38.

As shown in FIGS. 1c and 2, a concave, depressed cutout 40 is formed on the outer circumferential surface of the tip 30. In this embodiment, a channel opening 42 is formed on one side of the cutout 40, and an objective lens 44 and a light source 46 are disposed on another side of the cutout 40 for imaging. Both the objective lens 44 and the light source 46 are positioned adjacent to the channel opening 42. The tip 30 further comprises a nozzle 48 extending from a back wall surface 50 of the cutout 40. The nozzle 48 allows a stream of water, air, or the like to spray towards the outer surface of the objective lens 44 to clean the lens surface.

As depicted in FIGS. 2 and 3, tip 30 further includes a guide catheter 52 and a wire guide 56 disposed through the guide catheter 52. The tip 30 further includes an elevator 43 configured to receive the guide catheter and/or wire guide for elevating the guide catheter 52 or wire guide 56. As will be described in greater detail below, the elevator 43 includes a distal tip 112 disposed thereon. The distal tip 112 comprises aids to reduce the risk of damage, e.g., tearing or scraping, the wire guide 56. The distal tip 112 comprises a body 113 having lateral ridges or ribs 114 to aid in reducing the risk of damage to the wire guide 56.

In one embodiment, the elevator 43 is formed from an elastomeric material to prevent stripping of instruments used with the endoscope. In addition to preventing stripping, the elastomeric elevator allows a clinician to more firmly grasp and secure the distal end of an instrument or wire guide relative to the endoscope as compared to endoscopes having rigid elevators. For example, the elastomeric elevator can be formed from rubber. To avoid further stripping or otherwise damaging an instrument or wire guide a cuff can be provided with an elastomeric outer surface.

Figure 5:
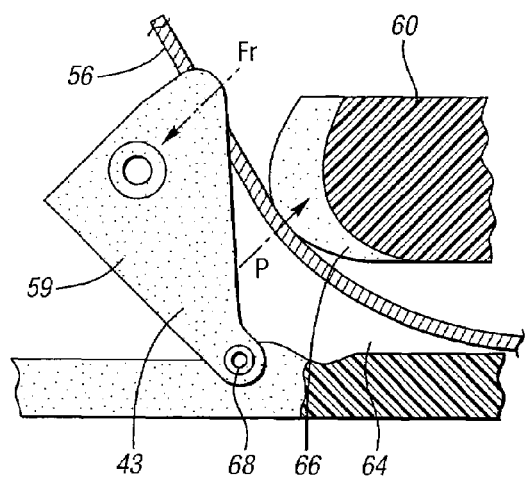
FIG. 5 is a cross-sectional view of the tip of the endoscope of FIG. 1, depicting a wire guide secured by an elevator.

FIGS. 3 and 5 illustrate that the endoscope tip 30 includes a cuff 60 as the main body of the tip 30, and a sleeve or cover 62 that covers the perimeter of the cuff 60. As shown, the cover 62 is formed using a nonconductive member such as any suitable polymeric material, e.g., high density polyethylene or polypropylene. In this embodiment, the cover 62 is attached to the cuff 60 by any suitable means, e.g., by adhesive bonding. The cuff 60 is in fluid communication with the working channel 63, which acts as a passageway for the insertion of the device, e.g., wire guide or catheter. Preferably, a passageway 64 is formed therethrough having an accommodation space 65 formed adjacent the cuff 60 and the tip cover 62.

In this embodiment, the channel 63 is formed through the tip 30 such that the tip opening of the treatment instrument is able to be disposed through the channel 63 defining an opening in the accommodation space 65. As shown in FIG. 3, the accommodation space 65 houses an elevator 43. The elevator 43 is used to orient medical instruments such as a catheter 52 (depicted in FIG. 2), or forceps, extending distally within the working channel 63. The elevator 43 preferably is also used to secure the distal end of the medical instrument or wire guide relative to the endoscope. A guide plane 69 for guiding a treatment instrument is formed from a groove with any desired shape formed in the treatment instrument elevator 43 to provide a connection with the insertion guide passageway 64. As shown in FIG. 3, the elevator turning support 68 is located off-center relative to the tip opening of the passageway 64. The elevator 43 is mounted such that the distal portion of the elevator pivots or rotates across within the accommodation space 65.

Figure 4:
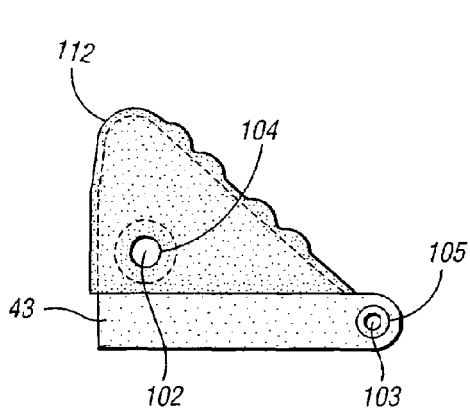
FIG. 4 is a side view of an elevator in accordance with one embodiment of the present invention.

In another embodiment, FIG. 4 illustrates the elevator 43 having transverse passageways 102 and 103 formed therethrough, each having optional metal sleeves 104 and 105, respectively, disposed thereon. The metal sleeves 104 and 105 are configured to provide transverse rigidity to the elevator. The proximal end of the elevator 43 is attached so as to pivot around the elevator turning support 68 provided to the cuff 60.

FIG. 3 further illustrates an elevator wire 90 connected to the elevator 43. In this embodiment, the elevator wire 90 is located at the operating portion 25 and extends through a guide tube 92 and a guide pipe 91 connected to the guide tube 92. The elevator wire 90 is in mechanical communication with the control system 14 so that manipulations at the control system 14 result in movement of the elevator wire 90 relative to the endoscope. FIG. 3 depicts (in phantom) movement of the elevator 43 when the elevator wire 90 is actuated at the control system 14, moving the position of the elevator 43 about the elevator turning support 68 as the elevator wire 90 is retracted or pulled.

In this embodiment, the elevator 43 is rotated about the elevator turning support 68 by manipulating or actuating the control system 14 to pull or retract the elevator wire 90. As shown in FIG. 5, the result moves the wire guide 56 in the direction of the arrow P and pushes the elevator 43 against the cuff 60. Because the wire guide 56 is formed from a relatively axially stiff material, it tends to remain straight when pushed against the cuff 60, creating a reactive force in the direction of the arrow Fr in FIG. 5. By means of this reactive force, the wire guide3. 56 is pressed against a wire guide catch groove. Moreover, as the elevator 43 and the cuff 60 compress against one another, the wire guide 56 is secured.

Figure 6:
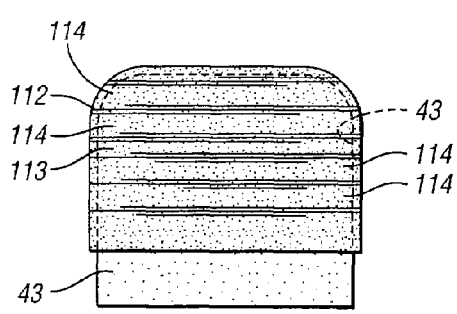
FIG. 6 is an elevated view of an elevator according to one embodiment of the present invention.
Figure 7:
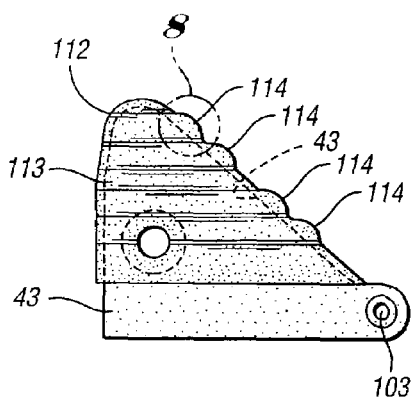
FIG. 7 is a side view of the elevator in FIG. 6 having engaging ribs according to one embodiment of the present invention.

FIGS. 6 and 7 illustrate the elevator 43 comprising a tip 112 disposed on the elevator 43 in accordance with one embodiment of the present invention. In this embodiment, the tip 112 is slidingly disposed directly over the elevator 43 and adhered thereon by any suitable means, e.g., sonic bonding, thermal bonding, or adhesive bonding. As shown, the tip 112 comprises a body 113 having a plurality of lateral ridges or ribs 114 formed thereon. The body 113 has an opening formed therethrough and is disposed over the elevator 43 with the lateral ridges 114 positioned thereacross to receive and contact the device. As shown in FIG. 7, the elevator 43 includes a transverse passageway 103 at the proximal end. As provided above with respect to FIG. 4, the proximal end of the elevator is attached so as to pivot around the elevator turning support 68. The elevator 43 and the tip 112 directly disposed thereon are configured to pivot about the elevator turning support 68 as one unit to engage the tip 112 with the elongate medical device.

As shown in FIGS. 6 and 7, the lateral ridges 114 are configured to contact and engage the device, e.g., wire guide or catheter, within the endoscope during usage thereof. The lateral ridges 114 aid in retaining and guiding the wire guide 56, while also reducing the risk of damage to the wire guide. This is accomplished due to the lateral structure of the ridges 114 and the composition thereof. The ridges 114 may take on any desirable or suitable formation to contact the device (e.g. wire guide).

In addition to reducing the risk of damage, the tip 112 allows a physician to more firmly grasp and secure the distal end of an instrument or wire guide relative to the endoscope as compared to endoscopes having bare, rigid elevators. To avoid further stripping or otherwise damaging an instrument or wire guide, cuff 60 can be provided with an elastomeric outer surface 66.

Moreover, the lateral ridges 114 may be made of any suitable material including elastomeric and polymeric materials, e.g., polytetrafluoroethylene (PTFE), polyethylene, polypropylene, perfluoroelastomer, fluoroelastomer, nitrile, neoprene, polyurethane, silicone, polytetrafluroethylene, styrene-butadiene, rubber, or polyisobutylene. The tip 112 may be made of any suitable material that will cooperate with the device to absorb and deform when in contact therewith, thereby reducing the risk of damage to the wire guide.

Figure 8A:
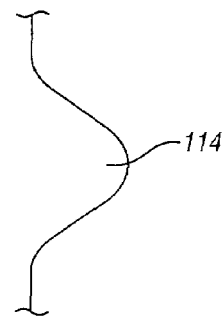
FIGS. 8a-8c are enlarged side views of the elevator in circle 8 of FIG. 7 in accordance with examples of the present invention.
Figure 8B:
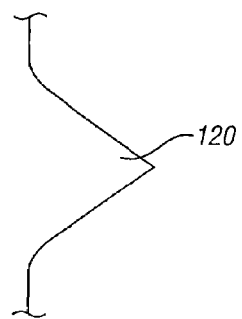
Figure 8C:
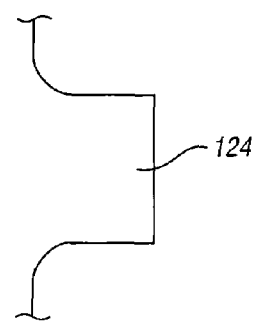

FIGS. 8a-8c further illustrate various configurations of ridges or ribs 114, 120, 124, respectively, formed on the elevator. As mentioned, the ridges 114 may take on any desirable or suitable shape for contact with the wire guide. As shown in FIGS. 8a-8c for example, the ridges 114, 120, 124 may have a cross-sectional shape that is semi-circular or arcuate (FIG. 8a), triangular (FIG. 8b), or rectangular (FIG. 8c).

Figure 9:
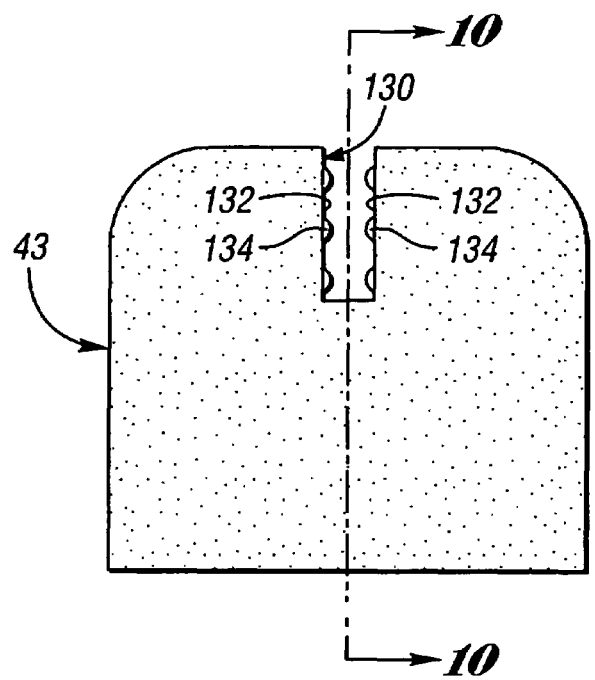
FIG. 9 is an elevated view of an elevator in accordance with one embodiment of the present invention.

In yet another embodiment, FIG. 9 illustrates the elevator 43 comprising a grasping slot 130 in accordance with one embodiment of the present invention. The grasping slot may take on any suitable shape or form for grasping of a medical device. In this embodiment, the grasping slot 130 is narrowly formed by inner sides 132 that define the grasping slot 130 through the elevator 43. Preferably, the grasping slot 130 is centrally formed through the elevator 43 for receiving a medical device (e.g., catheter or wire guide) and grasping the device during operation of the endoscope.

Figure 10:
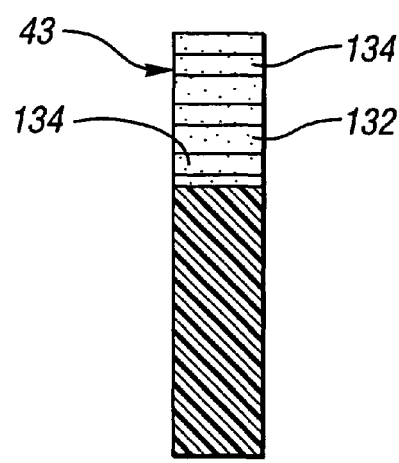
FIG. 10 is a cross-sectional view of the elevator in FIG. 9 taken along line 10-10 in accordance with one embodiment of the present invention.

FIGS. 9 and 10 illustrate the elevator having inner sides 132 in accordance with one embodiment of the present invention. As shown, inner sides 132 include side grasping members 134 formed thereon. In this embodiment, side grasping members 134 are ridges or ribs that are oppositely formed laterally across each of the inner sides 132. Of course, the side grasping members 134 may be formed on either or both of the inner sides, in any suitable shape, and in staggered configuration. For example, the inner grasping members may be formed longitudinally or in different patterns without falling beyond the scope or spirit of the present invention.

In use, the control system of the endoscope may be manipulated to actuate the elevator, moving the elevator to engage the medical device, e.g., catheter or wire guide. By force, the medical device is worked through the grasping slot 130 of the elevator 43, thereby engaging the medical device with the inner sides 132 of the elevator 43. The side grasping members 134 engage the device and, due to the polymeric material of the elevator 43, partially deform and absorb the device to reduce the risk of scraping thereof. In use, the side grasping members 134 receive the medical device when disposed within the slot for enhanced grasping and reduced risk of scraping of the medical device.

In addition to reducing the risk of damage, the formation of the slot allows a physician to more firmly grasp and secure the distal end of an instrument or wire guide relative to other endoscope. To avoid further stripping or otherwise damaging an instrument or wire guide, cuff 60 can be provided with an elastomeric outer surface 66.

Figure 11A:
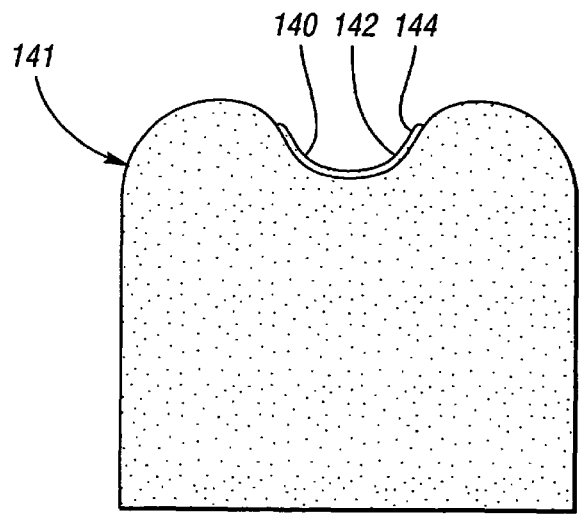
FIGS. 11a-11c are elevated views of elevators in accordance with other embodiments of the present invention.
Figure 11B:
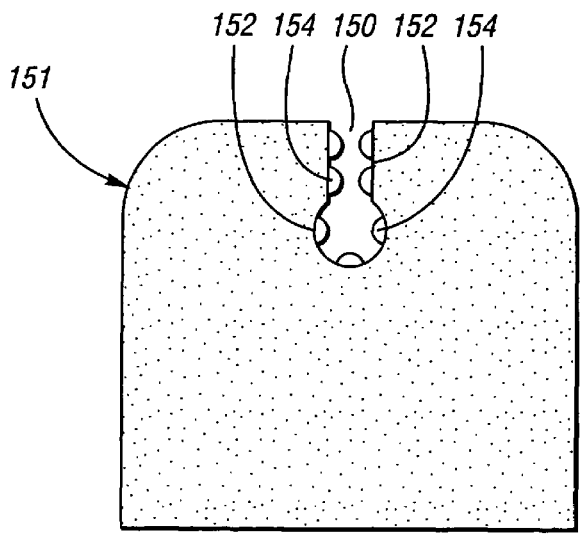
Figure 11C:
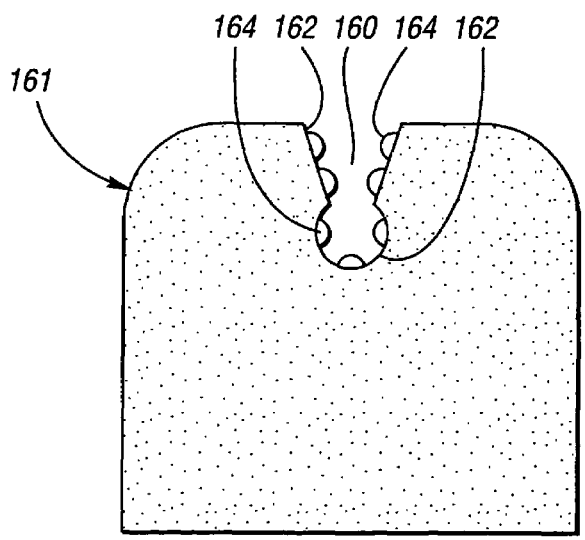

FIGS. 11a-11c further illustrate various configurations of grasping slots 140, 150, 160 formed through the elevator. As mentioned, the grasping slots may take on any desirable or suitable shape for grasping of a medical device of an endoscope. For example, as shown in FIG. 11a, the grasping slot 140 of elevator 141 may have a cross-sectional shape that is semi-circular or arcuate. In this embodiment, the grasping slot 140 has an arcuate side 142 that defines the grasping slot 140. As shown, the arcuate side 142 includes grasping member 144 formed thereon for grasping the medical device.

FIG. 11b illustrates grasping slot 150 of elevator 151 in accordance with another embodiment of the present invention. As shown, the grasping slot 150 has inner and arcuate sides 152 that define the slot 150. In this embodiment, the sides 152 include grasping members 154 formed thereon for grasping the medical device.

FIG. 11c illustrates grasping slot 160 of elevator 161 in accordance with yet another embodiment of the present invention. As shown, the grasping slot 160 has tapered and arcuate sides 162 that define the slot 160. In this embodiment, the sides 162 include grasping members 164 formed thereon for grasping the medical device.

While the present invention has been described in terms of preferred embodiments, it will be understood, of course, that the invention is not limited thereto since modifications may be made to those skilled in the art, particularly in light of the foregoing teachings.

The invention claimed is:

1. A grasping apparatus for use with an elevator of an endoscope having enhanced grasping features for grasping an elongate medical device, the apparatus comprising:
a grasping tip configured to be disposed on the elevator of the endoscope for grasping the elongate medical device, the endoscope having an endoscope tip having an outer surface and an accommodation space formed within the endoscope tip, the elevator being pivotally mounted within the accommodation space of the endoscope via an elevator turning support, the grasping tip having a body including a grasping surface and an opening formed through the body to slidingly receive the elevator directly therein, the opening of the body being configured to be disposed directly over the elevator wherein the elevator and the grasping tip disposed thereon are configured to pivot about the elevator turning support as one unit to engage the grasping tip with the elongate medical device.

2. The apparatus of claim 1 wherein the grasping tip is made of polymeric material.

3. The apparatus of claim 2 wherein the polymeric material includes at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

4. The apparatus of claim 1 wherein the grasping tip comprises at least one ridge formed on the body.

5. The apparatus of claim 4 wherein each ridge has a predetermined shape for enhanced grasping and reduced scraping of the medical device.

6. The apparatus of claim 5 wherein the predetermined shape includes at least one of the following shapes: triangular, semi-circular, and rectangular.

7. The apparatus of claim 4 wherein the at least one ridge is formed laterally across the body relative to the elevator.

8. The apparatus of claim 4 wherein the at least one ridge is formed longitudinally across the body relative to the elevator.

9. The apparatus of claim 1 wherein the grasping tip is disposed on the elevator with adhesive.

10. The apparatus of claim 1 wherein the body comprises a lip defining the opening through which the elevator is received.

11. The apparatus of claim 1 wherein the grasping surface and opening of the body of the grasping tip cooperates with the elevator of the endoscope for enhanced grasping of the elongate medical device.

12. An endoscopic grasping assembly for an endoscope having enhanced features for grasping and reducing damage of an elongate medical device, the assembly comprising:
an insertion tube extending to a distal tip having an elevator and a control system in communication with the insertion tube and the elevator for movement of the insertion tube and elevator during operation of the endoscope; and
a grasping tip disposed on the elevator for grasping the elongate medical device, the endoscope having an endoscope tip having an outer surface and an accommodation space formed within the endoscope tip, the elevator being pivotally mounted within the accommodation space of the endoscope via an elevator turning support, the grasping tip having a body including a grasping surface and an opening formed through the body to slidingly receive the elevator directly therein, the opening of the body being disposed directly over the elevator wherein the elevator and the grasping tip disposed thereon are configured to pivot about the elevator turning support as one unit to engage the grasping tip with the elongate medical device.

13. The assembly of claim 12 wherein the grasping tip is made of polymeric material.

14. The assembly of claim 13 wherein the polymeric material includes at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

15. The assembly of claim 12 wherein the grasping tip comprises at least one ridge formed on the body.

16. The assembly of claim 15 wherein each ridge has a predetermined shape for enhanced grasping and reduced scraping of the medical device.

17. The assembly of claim 16 wherein the predetermined shape includes at least one of the following shapes: triangular, semi-circular, and rectangular.

18. The assembly of claim 12 wherein the elevator is comprised of elastomeric material.

* * * * *